United States Patent [19]

Gluschenko et al.

[11] Patent Number: 4,677,864
[45] Date of Patent: Jul. 7, 1987

[54] SYSTEM FOR AUTOMATIC SAMPLING AND SAMPLE CONVEYANCE FOR ANALYSIS

[75] Inventors: Nikolai N. Gluschenko; Vladislav V. Golikov; Viktor A. Emelyanov, all of Sverdlovsk, U.S.S.R.

[73] Assignee: Vsesojuzny Nauchno-Issledovatelsky I Konstruktorsky Institut Tsvetmetavtomatika, Sverdlovsk, U.S.S.R.

[21] Appl. No.: 788,469

[22] Filed: Oct. 17, 1985

[30] Foreign Application Priority Data

Apr. 6, 1981 [SU] U.S.S.R. ............................ 3272538

[51] Int. Cl.[4] .......................... G01N 1/20; G01N 1/14
[52] U.S. Cl. .............................. 73/863.51; 73/863.54
[58] Field of Search ................. 73/863.51, 863.54, 864

[56] References Cited

U.S. PATENT DOCUMENTS

| | | | |
|---|---|---|---|
| 2,893,602 | 7/1959 | Barber et al. | 73/863.54 X |
| 3,464,272 | 9/1969 | Griffith et al. | 73/863.54 X |
| 3,468,169 | 9/1969 | Putnam | 73/864 X |
| 3,638,476 | 2/1972 | Paterson et al. | 73/863.51 X |
| 3,999,438 | 12/1976 | Sundkvist et al. | 73/863.51 X |
| 4,156,507 | 5/1979 | Gokabowski et al. | 73/863.54 |
| 4,432,674 | 2/1984 | Klose et al. | 73/863.54 X |

FOREIGN PATENT DOCUMENTS

| | | | |
|---|---|---|---|
| 750319 | 7/1980 | U.S.S.R. | |
| 802838 | 2/1981 | U.S.S.R. | 73/863.54 |

OTHER PUBLICATIONS (Translated from Russian) Definition of Cyclone; Polytechnical Dictionary; p. 554, 1976, Chief editor N. I. Artobolevsky.
(Translated from Russian) "Methods of Analysis and Laboratory Equipment System for Conveying Samples of Slurry for Analysis in KRF-13 Quantometer"; *Abstract Journal Innovative Proposals and Inventions;* No. 6, (342), pp. 8-10, 1980, V. N. Yanchevsky et al.
(Translated from Russian) "System for Automatic Sampling and Slurry Sample conveyance" *Tsvetnaya Metallurgia;* No. 20, pp. 35-37; N. N. Gluschenko et al.

*Primary Examiner*—Stewart J. Levy
*Assistant Examiner*—Tom Noland
*Attorney, Agent, or Firm*—Ladas & Parry

[57] ABSTRACT

A system for automatic sampling and sample conveyance for analysis, comprising a sampler having a slurry sampling member having a drain in the form of a flexible hose, a compressed air line, the flexible hose being connected, via a controlled valve, to a chamber for accumulation and dispatch of samples having check valves and an outlet which is connected, via a conveying line, to a sample receiver. The system is provided with a metering receptacle connected to the flexible drain hose and mounted at the inlet of the chamber and connected, via a controlled valve, to a water supply line, the capacity of the metering receptacle being commensurable with the capacity of the chamber, and the controlled valves being connected in parallel with each other.

1 Claim, 2 Drawing Figures

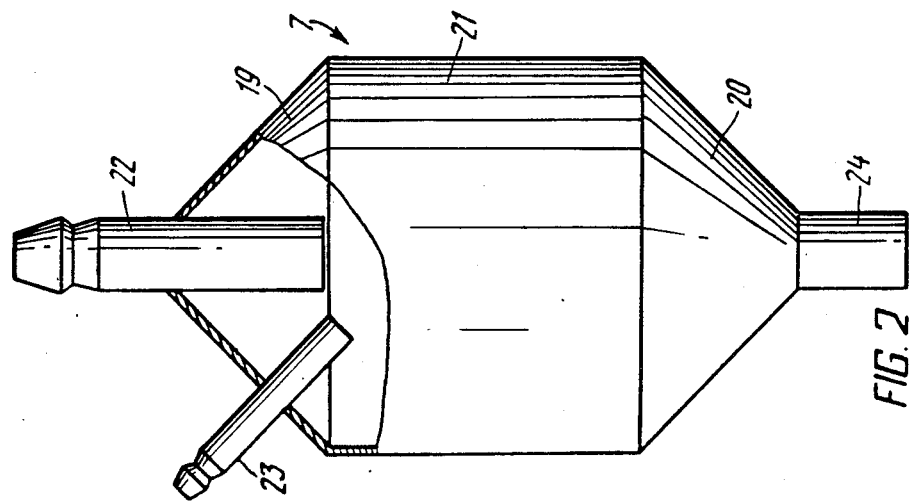
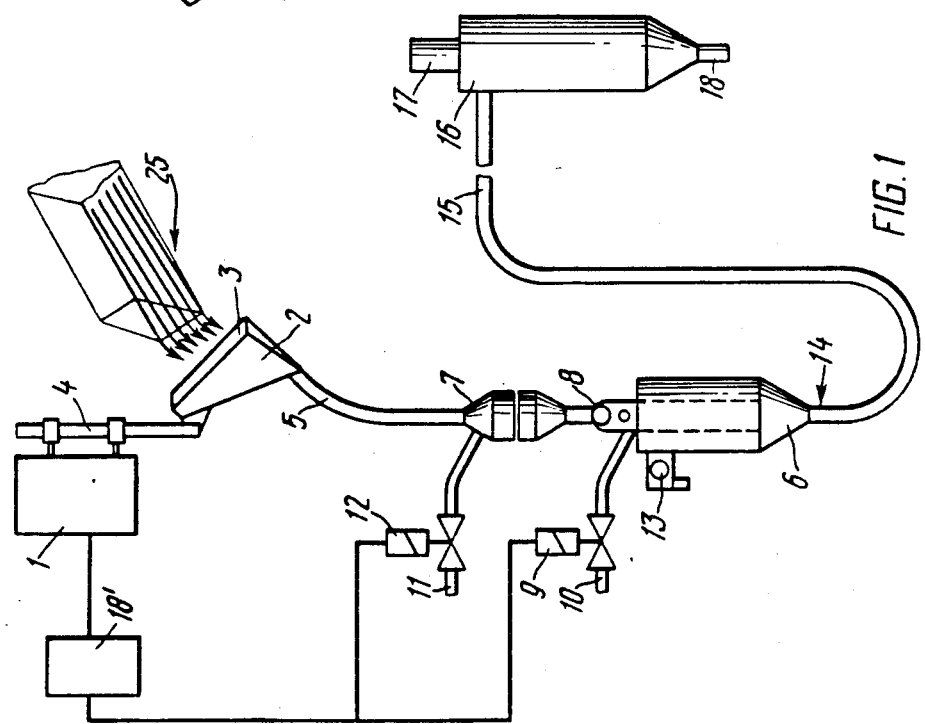

SYSTEM FOR AUTOMATIC SAMPLING AND SAMPLE CONVEYANCE FOR ANALYSIS

FIELD OF THE ART

The invention relates to the concentration processes, and in particular, it deals with the analytical control of samples of solutions and slurries at metallurgical, chemical and similar plants, and more specifically, the invention relates to systems for automatic sampling and sample conveyance for analysis.

BACKGROUND OF THE INVENTION

Known in the art is a system for automatic sampling and slurry sample conveyance for analysis (cf. Yanchevsky V. N. et al., System for Conveying Slurry Samples for Analysis in a Quantometer KRF-13. (in Russian), Innovative Proposals and Inventions, No. 6, (342), pp. 8–10, Moscow, 1980), comprising samplers installed on slurry lines conveying products being analyzed, a sampling member of a slurry sampler being connected to a receiving sump of a rotary pump by means of a flexible hose. The pump, in the analysis mode, pumps in the sample through a conveying line to a pressure tank which is installed in an express laboratory over the cells of an analyzer. The receiving sump of the pump has a check drain funnel, and the flexible hose of the sampler is connected to a pneumatic membrane actuator by means of a pull member in such a manner that in one position (in the analysis mode) the slurry is fed from the sampler to the pump sump and in the other position (in the washing mode), to the drain funnel. In addition, a water supply pipeline having a shut-off valve connects to the pump sump. For washing the sample conveyance system, the pneumatic actuator directing the slurry sample to the drain funnel and the shut-off valve starting water supply to the receiving sump of the pump are actuated simultaneously. Water flowing through the conveying line and other devices of the system in the express laboratory washes them. After the washing is over, the system is switched back to the analysis mode.

However, with such a system, washing of the drain hose and sampling aperture of the sampler is impossible. In practice, it is these elements that are most prone to clogging which is not infrequently the cause of clogging of the drain hose and failure of the system. Gradual accumulation of slurry residue in the drain hose and their subsequent separation from the hose wall results in a substantial contamination of a sample being analyzed. In addition, the conveying line should be completely filled for washing it so that a large amount of water is required, whereas efficiency of washing depends on water velocity thus making it necessary to install a high capacity pump.

Also known in the art is a system for automatic sampling and sample conveyance in sampling slurries (cf. Yu. A. Baranov, System for Automatic Sampling and Slurry Sample Conveyance (in Russian), Jr. Tsvetnaya Metallurgia, No. 20, 1982, pp, 35–37), comprising a sampler having a slurry sampling member in the form of an apertured blade which is mounted at an overfall of a process slurry flow being controlled. The drain of the apertured blade of the sampler is connected by means of a flexible hose to a chamber for accumulation and dispatch of samples through a first check valve. The chamber for accumulation and dispatch of samples is connected, via an electrically controlled valve, to a compressed air supply line, and, via a conveying line, to a sample receiver. In addition, to ensure that the the volume of the sample being dispatched should be always the same, the chamber for accumulation and dispatch of samples is filled with water to the overflow level, water being continuously supplied through a second check valve. During operation of the system, a single sample received by a sampler during one cycle of its operation is fed under gravity through the flexible hose to the chamber for accumulation and dispatch of samples. The accumulated sample is dispatched and conveyed by admitting compressed air to the chamber by actuating the electrically controlled valve. The sample is admitted from the conveying line to the sample receiver and then to a circulation circuit for an X-ray spectral analysis.

The chamber for accumulation and dispatch of samples, conveying line and sample receiver are washed by feeding compressed air, upon actuation of the electrically controlled valve, to the chamber for accumulation and dispatch of samples immediately after it has been filled with water.

This system calls for a large water consumption (more than 150 l/h), yet there is no provision for washing of the sampling aperture and flexible drain hose. It is these parts of the system that are most prone to clogging with slurry thus not only resulting in less reliability of the sample analysis data because the sample is not quite representative, but also causing clogging of the sampler aperture and the hose and up to the complete failure of the system.

SUMMARY OF THE INVENTION

It is an object of the invention to improve reliability of the system in operation by eliminating clogging of various parts of the system.

Another object of the invention is to make a sample taken for analysis more representative by ensuring constant dimensions of the sampler aperture, hence, uniform sampling through the aperture.

A further object of the invention is to lower water consumption owing to its cyclic supply.

The invention essentially resides in that in a system for automatic sampling and sample conveyance for analysis, comprising a sampler having a slurry sampling member, having a drain in the form of a flexible hose connected to a chamber for accumulation and dispatch of samples having check valves and connected to a water supply line and, via a controlled valve, to a compressed air supply line, a sample receiver which is connected, via a conveying line, to the outlet of the chamber for accumulation and dispatch of samples, and a command device electrically connected to the sampler and controlled valve. According to the invention, also provided is a metering receptacle installed at the inlet of the chamber for accumulation and dispatch of samples, and an additional controlled valve mounted between the water supply line and the metering receptacle, the metering receptacle being of a capacity which is close or equal to the capacity of the chamber for accumulation and dispatch of samples, and the controlled valves being connected in parallel with each other.

The system according to the invention makes it possible to effect a cyclic washing of the flexible hose and slurry sampling member when the additional valve is opened so as to avoid clogging thereof, hence eliminating failures of the system, the representativeness of samples taken for analysis also being improved. In addition, water consumption is lowered because it is unnecessary to supply water continually to the chamber for accumulation and dispatch of samples.

DESCRIPTION OF THE DRAWING

These and other objects and advantages of the invention will become apparent from the following detailed description of an embodiment thereof with reference to the accompanying drawing, in which:

FIG. 1 shows a structural diagram of a system for automatic sampling and sample conveyance for analysis according to the invention;

FIG. 2 is a structural embodiment of a metering receptacle according to the invention.

DETAILED DESCRIPTION OF THE INVENTION

A system for automatic sampling and sample conveyance comprises a sampler 1 having a slurry sampling member 2 in the form of an apertured blade 3 mounted on an arm 4 of the sampler 1, which may be similar to that described in USSR Inventor's Certificate No. 802838. The sampler according to USSR Inventor's Certificate No. 802,838 comprises a casing on which there is mounted an electric drive with the gearbox and guides with a carriage movable thereon and rigidly coupled to an arm 4 which carries a slurry sampling member 2. The carriage is set in motion by the electric drive with the gearbox via a bushing-and-roller chain transmission. The electric drive of the sampler is periodically turned on by a control means 18'. For draining slurry, the slurry sampling member 2 is connected, via a flexible hose 5, to an inlet of a chamber 6 for accumulation and dispatch of samples through a metering receptacle 7. At the inlet of the chamber 6 is installed a first check valve 8. The chamber 6 is connected, via the first check valve 8 and also via a valve 9 installed at the inlet of the chamber 6, to a line 10 for compressed air supply. The chamber 6 is also connected to a line 11 for supplying water through the metering receptacle 7 by means of an additional valve 12. The chamber 6 is provided with a second check valve 13 for discharging an excess of water. An outlet 14 of the chamber 6 connects, via a conveying line 15, to a sample receiver 16 having pipes 17 and 18 for discharging waste air and liquid sample (slurry) for analysis, respectively, the analysis being conducted, e.g. in an X-ray spectral analyzer (not shown). The design of the chamber 6 for accumulating and dispatch of samples is known in the art (cf. USSR Inventor's Certificate No. 750319).

The sample receiver 16 comprises a widely known cyclone (cf. Polytechnical Dictionary (in Russian), Ed. by N. I. Artobolevsky, M., Sovetskaya Entsiklopedia Publishing House, 1976, p. 554). A slurry and air mixture from the conveying line 15 is admitted to the receiver 16 wherein, owing to an abrupt and substantial volume increase (expansion) and lowering of velocity, the slurry flows down through the pipe 18, and the waste air escapes through the upper pipe 17.

The system also comprises a command device 18' which generally comprises a well known electric master controller having an electric motor with a reduction gearing having a shaft on which is mounted a cam and contact means for closing contacts in such a manner as to effect control in a pre-set sequence (not shown in the drawings). The outputs of the command device 18' are connected to an actuator means (not shown) of the sampler 1 and to the controlled valves 9 and 12. In order to ensure optimum conditions for operation of the system, the capacities of the metering receptacle 7 and chamber 6 are about equal to each other.

The metering receptacle 7 (FIG. 2) comprises a casing in the form of two oppositely mounted cones 19 and 20, and a cylinder 21. An inlet pipe 22 is welded into the upper cone 19 for admitting a slurry sample from the blade of the sampler 1 and for washing the blade and flexible hose 5 (FIG. 1), and there is also provided a pipe 23 (FIG. 2) for water supply, which is connected to the electrically controlled valve 12 (FIG. 1). A sample or accumulated water is drained through the lower cone 20 and a pipe 24 which is connected to the inlet of the sample accumulation chamber 6 (FIG. 1).

The system for automatic sampling and sample conveyance according to the invention functions in the following manner.

In the initial position, the controlled valves 9 and 12 are closed, the check valves 8 and 13 are open, the chamber 6 is filled with water to the level of the overflow opening of the check valve 13, and the sampling member 2 of the sampler 1 is ready to take a sample. Taking single samples in the system is effected by the sampler 1 following a command from the command device 18'. A single sample taken from the process flow (the flow direction is shown by arrows 25) is admitted, through the flexible hose 5 and metering receptacle 7, to the chamber 6 wherein several individual samples are regularly accumulated. The incoming samples displace water available in the chamber 6 through the overflow opening of the check valve 13 so that an accumulated sample of one and the same volume will be conveyed for analysis. The sample is dispatched and conveyed following a command from the command device 18' by feeding compressed air to the chamber 6 when the controlled valve 9 is opened. Under the action of compressed air, the check valves 8 and 13 are closed, and the sample is fed through the conveying line 15 to the sample receiver 16 wherein the conveying air is separated from the sample, and the sample is prepared for analysis. Concurrently with the opening of the controlled valve 9, the additional controlled valve 12 is opened to supply vater under pressure to the metering receptacle 7. Since the check valve 8 is closed, water will fill-up the metering receptacle 7 and will flow through the flexible hose 5 and apertures 3 of the slurry sampling member 2 so as to wash these elements of the system. After the sample has been conveyed, and following a command from the command device 18', the valves 9 and 12 are simultaneously closed so as to interrupt compressed air and water supply to the metering receptacle 7. The check valve 8 is opened, and water available in the metering receptacle 7 and flexible hose 5 will fill-up the chamber 6 which has the capacity commensurable with that of the metering receptacle 7. On the one hand, this provides a guarantee of one and the same volume of samples being conveyed for analysis with complete filling of the chamber 6 up to the overflow level and, on the other hand, water consumption is minimized. Water supply through the metering receptacle 7 makes it possible to isolate the water supply line 11 from the chamber 6 thus preventing it from being filled with water under pressure because otherwise a gauge water pressure in the chamber 6 would cause closure of the check valve 8 at the inlet thereof thus hampering admission of a sample to the chamber 6. After a certain time interval (of about one minute) set-up by the command device 18', the controlled valves 9 and 12 are again actuated and restart the supply of water and compressed air, the valve 8 being closed. Water admitted to the metering receptacle 7 will flow through the flexible hose 5 and sampling member 2 to wash these parts of the system once again. Water present in the chamber 6 is conveyed under the action of compressed air through the conveying line 15 to the sample receiver 16 to wash these parts of the system. When the sample has been conveyed, the controlled valves 9 and 12 are closed to interrupt supply of water and compressed air. The check valve 8 is thus opened, and water present in the metering receptacle 7 and in the flexible hose 5 fills the chamber 6. The system is brought back to the initial state. The cycle is then repeated at 15–30 minutes intervals.

Use of the invention, owing to the cyclic washing, substantially completely eliminates clogging of the slurry sampling member 2, i.e. the aperture of the blade 3, with slurry so that the geometrical configuration of the aperature 3 remains unchanged thus making it possible to take samples from the flow of slurry which are fully representative. In addition, washing of the flexible hose 5 with water is ensured so as to avoid danger of contamination of following samples with residues of the preceding samples. This facility improves reliability of the system in operation and representativeness of samples taken and conveyed for analysis and results in a lower water consumption (up to 25 l/h) and reduction of operation cost.

The invention may be used at concentration factories in the metallurgical and mining industries and in other industries.

We claim:

1. A system for automatic sampling and sample conveyance for analysis, comprising:
    a sampler having a slurry sampling member;
    a flexible hose having two ends and designed for draining slurry from said slurry sampling member;
    a metering receptacle having a sample inlet, a compressed air inlet, and an outlet;
    said flexible hose having one said end thereof connected to said slurry sampling member and said other end connected to said slurry inlet of said metering receptacle;
    a water supply line connected to another inlet of said metering receptacle;
    a chamber for accumulation and dispatch of samples having an inlet for the admission of slurry and compressed air, a first outlet for dispatching slurry, and a second outlet for draining an excess of water;
    a first check valve mounted at said inlet of said chamber for accumulation and dispatch of samples;
    a second check valve mounted at said second outlet of said chamber for accumulation and dispatch of samples;
    said metering receptacle being connected to said first inlet of said chamber for accumulation and dispatch of samples through said first check valve;
    a compressed air supply line connected to said inlet of said chamber for accumulation and dispatch of samples through a first controlled valve;
    an additional controlled valve mounted between said water inlet of said metering receptacle and said water supply line;
    a conveying line for conveying samples, having two ends,
    a sample receiver having an inlet for receiving slurry;
    said conveying line having one said end thereof connected to said first outlet of the chamber for accumulation and dispatch of samples and the other said end thereof connected to said inlet sample receiver;
    a command device having two outputs;
    one said output of the command device being electrically connected to said sampler;
    said other output of the command device being connected to said controlled valves;
    said controlled valves being connected in parallel with each other;
    capacities of said metering receptacle and said chamber for accumulation and dispatch of samples being about equal to each other.

* * * * *